United States Patent
Dolatkhani et al.

(10) Patent No.: US 7,534,262 B1
(45) Date of Patent: May 19, 2009

(54) BIMATERIAL INTRAOCULAR IMPLANT AND PROCESS FOR MAKING THE IMPLANT

(75) Inventors: Marc Dolatkhani, Talence (FR); Alain Deffieux, Talence (FR)

(73) Assignee: Ioltechnologie-Production, La Rochelle (FR)

( * ) Notice: Subject to any disclaimer, the term of this patent is extended or adjusted under 35 U.S.C. 154(b) by 801 days.

(21) Appl. No.: 09/486,065

(22) PCT Filed: Jun. 21, 1999

(86) PCT No.: PCT/FR99/01482

§ 371 (c)(1),
(2), (4) Date: Mar. 30, 2000

(87) PCT Pub. No.: WO99/65422

PCT Pub. Date: Dec. 23, 1999

(30) Foreign Application Priority Data

Jun. 19, 1998 (FR) .................................. 98 07778

(51) Int. Cl.
*A61F 2/16* (2006.01)

(52) U.S. Cl. ..................................... 623/6.56; 623/6.11
(58) Field of Classification Search ........ 623/6.11–6.64
See application file for complete search history.

(56) References Cited

U.S. PATENT DOCUMENTS

| 3,391,224 | A | * | 7/1968 | Sherr et al. ................... 525/41 |
| 4,813,956 | A | | 3/1989 | Gupta |
| 4,995,879 | A | | 2/1991 | Dougherty |
| 5,282,854 | A | * | 2/1994 | Yagi et al. ................... 623/6.56 |
| 5,326,506 | A | * | 7/1994 | Vanderbilt ................... 623/6.56 |
| 5,674,284 | A | | 10/1997 | Chang et al. |
| 5,693,095 | A | * | 12/1997 | Freeman et al. ............. 623/6.56 |
| 5,762,836 | A | * | 6/1998 | Bos et al. ..................... 264/1.7 |
| 6,011,082 | A | * | 1/2000 | Wang et al. .................. 523/107 |
| 6,267,784 | B1 | * | 7/2001 | Benz et al. ................... 623/6.59 |
| 6,271,332 | B1 | * | 8/2001 | Lohmann et al. ........... 623/5.16 |

FOREIGN PATENT DOCUMENTS

| EP | 0 492 126 | 7/1992 |
| EP | 0 590 926 | 4/1994 |
| EP | 0 637 503 | 2/1995 |
| JP | 5-269 191 | 10/1993 |

* cited by examiner

Primary Examiner—Brian E. Pellegrino
(74) Attorney, Agent, or Firm—Young & Thompson

(57) ABSTRACT

The invention concerns an implant forming an intraocular lens comprising a central optical part, a globally circular outline, at least partly made of a flexible material and a haptic part, at said optical part periphery, made at least partially of a rigid material. Said implant has a single-piece structure. The implant rigid material is a shape modified by at least one process selected among chemical reactions and polymerisation reactions of the starting flexible material, for example based on PMMA-PHMA, cross-linked by adding a multifunctional agent such as diethyleneglycol dimethacrylate.

20 Claims, 1 Drawing Sheet

BIMATERIAL INTRAOCULAR IMPLANT AND PROCESS FOR MAKING THE IMPLANT

Figure 2:
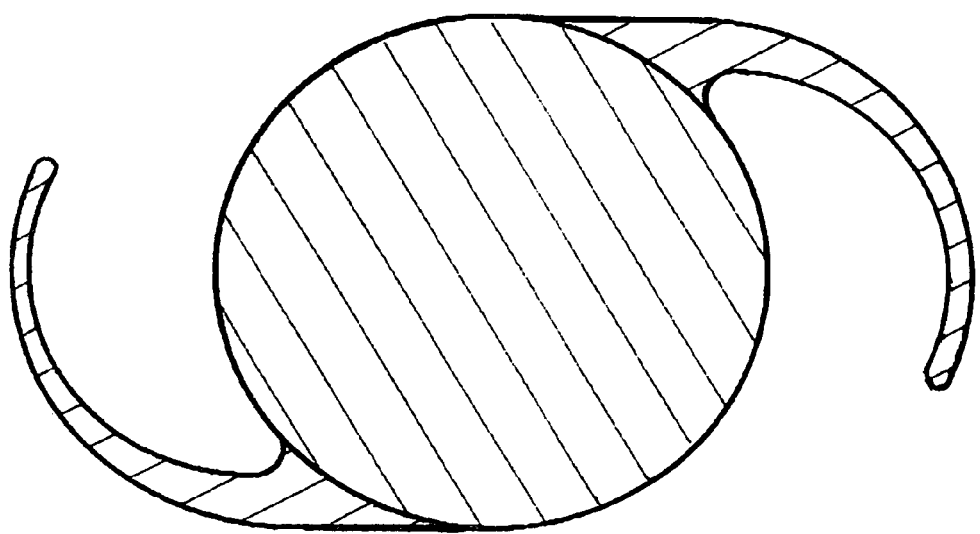

The invention relates to an implant forming an intraocular lens and intended for implantation in the eye of a patient who is lensed or lensless (aphacic) following extraction of the opacified natural crystalline lens, or for correction of refractive ametropias.

In the case of an eye which is aphacic following opacification of the natural crystalline lens (cataract) the implant is generally placed in the posterior chamber in the capsular sac situated behind the iris, but can also be implanted in the ciliary sulcus or in the anterior chamber in front of the iris.

In the case of a lensed eye, implantation with the aim of correcting a refractive ametropia generally takes place in front of the iris, since the capsular sac is still occupied by the natural crystalline lens. However, it is also possible to envisage implantation behind the iris, between the iris and the crystalloid substance.

All implants which form an intraocular lens include a central optical part, whose overall contour is circular, and a haptic part, which is disposed at the periphery of the optical part and is intended to be positioned so as to stabilize the implant.

Numerous types of implants referred to as rigid implants are known, commonly being made of polymethyl methacrylate (PMMA). Such implants require a major sclerocorneal incision and risk damaging the ocular tissues.

In order to overcome this problem, attempts has been made to develop implants referred to as flexible implants, made in particular of hydrogel, hydroxyethyl methacrylate (HEMA) and flexible acrylic material. These implants can be folded or rolled up on themselves, in particular about a diametral axis of the optical part, for introduction via a small incision, allowing rapid sclerocorneal cicatrization.

One known flexible implant comprises a central, lens-forming optical element and two haptic elements at the periphery of the optical element. With flexible implants of this type, made in particular of hydrogel, hydroxyethyl methacrylate (HEMA) and flexible acrylic material, the problems of positioning and stabilization are more difficult to solve than with other, rigid implants.

In the case of implantation following extraction of the opacified crystalline lens, it is known that the implants are difficult to maintain in a stable position owing to the fact that the cut made in the anterior capsule is not, in practice, perfectly centered. The cut edge of said anterior capsule therefore covers the haptic branches to differing extents. Consequently, in the weeks following the operation, the axial component of the force which is exerted by contraction of the cut edge of the anterior capsule on a haptic element can vary depending on the position of the implant in the capsular sac. One of the haptic branches can be drawn backward, such that correct positioning of the implant in the capsular sac is not ensured.

Likewise, in the case of implantation in a lensed eye, the position of the implant must be stable in order to prevent any displacement or contact of certain parts of the implant with the internal eye tissues.

In an attempt to resolve these difficulties, the production has been considered of bimaterial intraocular implants, i.e., implants comprising an optical part in a first material, generally flexible, allowing folding and rolling, and haptic parts made of a second, rigid material, such as PMMA, in order to ensure a good hold and stability of the lens following implantation.

EP208546 describes an implant comprising an optical part made of PMMA and a haptic part, made of polypropylene, at the periphery of the optical part. Subsequently, mechanical integration is ensured by virtue of a laser beam which softens the material, which subsequently hardens after cooling. An operation of this kind is complicated and considerably increases the production costs of the lens.

Also known is an intraocular lens comprising an optical part made of flexible material and a haptic part made of rigid material, such as PMMA, which ensures bonding by fusion of the two materials in the contact zone. The process of manufacture of such a lens likewise exhibits disadvantages. Specifically, the positioning of the haptic parts relative to the periphery of the optical part is not easy, so leading to an increase in the manufacturing costs of the lens. Defects may also become evident at the junction zone, bringing with them a risk of separation of the haptic part.

One object of the invention is to provide an implant which forms an intraocular lens and which suffers neither from the disadvantages of monobloc intraocular lenses made from rigid material or flexible material nor from the disadvantages of bimaterial implants which involve the fusion or assembly of the haptic and optical parts.

The implant for a lensed or aphacic eye, according to the invention, comprises:

an optical part and a haptic part, the optical part being made at least partially of flexible material and the haptic part being made at least partially of rigid material, wherein the structure of said implant is monobloc.

According to one provision of the invention, the rigid material is the flexible material in a form modified by at least one reaction selected from chemical reactions and polymerization reactions.

Figure 1:
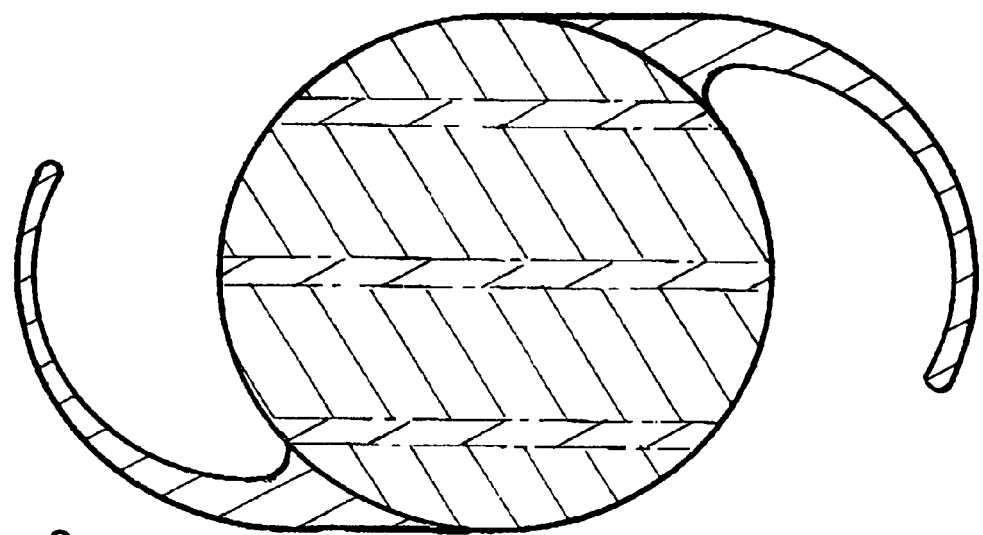

FIG. 1 is a sectional view of an intraocular implant comprising an optical part made entirely of flexible material and a haptic part made entirely of relatively rigid material; and FIG. 2 is a section view of an intraocular implant similar to that of FIG. 1 in which the optical part is made of alternating strips of flexible and rigid material and the haptic part is made of rigid material.

The optical part can be made entirely of flexible material or can comprise one or more strips made of flexible material alternating with strips made of rigid material. Whatever the embodiment, the rigid material of the optical part allows said part to be folded or rolled in order that it can be introduced through a small incision.

In accordance with one variant embodiment, the optical part comprises a zone made of rigid material which adjoins the haptic part and is in continuity with the rigid material of the optical part.

In practice, the haptic part will be made entirely of rigid material. It may comprise one (or more) zone(s) made of flexible material.

The flexible material of the implant which forms an intraocular lens is generally hydrophilic, but may also be selected from polysiloxanes, which are not (generally) hydrophilic; their flexibility is due to a very low glass transition temperature (Tg).

The flexible material of the implant which forms an intraocular lens is advantageously selected from crosslinked polymer and copolymer materials such as, for example, random methyl methacrylate-hydroxymethyl methacrylate (MMA-HMA) copolymers crosslinked by the addition of a polyfunctional agent such as diethylene glycol dimethacrylate. The flexible material of the lens is based, for example, on PMMA-PHMA copolymers, crosslinked with diethylene glycol dimethacrylate.

The implant of the present invention is notable in that it is both monobloc and bimaterial. The rigid material results from a structural modification of the flexible material. The implant of the invention thus consists of two materials, a flexible material and a rigid material, without any fusion or assembly of these two materials.

The combination of the two features, monobloc and bimaterial, in the implant according to the invention gives it a reliability and a longevity which are superior to those of known bimaterial lenses made by fusion or assembly.

The process of manufacturing the implant comprises a first step of producing a preform (or blank) which can be shaped into an intraocular lens from a flexible monobloc starting material, a step of shaping of said preform into an intraocular lens, characterized in that said process further comprises a step of structurally modifying at least one zone of the preform which it is intended should become rigid.

In accordance with one provision of the invention, the step of structural modification comprises a phase of impregnating the zone of the preform with reactive organic compounds.

The step of structurally modifying the starting material can be carried out by deploying a chemical reaction and/or a polymerization reaction.

In a first embodiment of the invention, the shaping step, which is commonly carried out by machining, precedes the step of structurally modifying the starting material. In such a case, it is appropriate to carry out a step of protecting at least one zone of the preform which it is intended should remain flexible, prior to the step of structurally modifying the starting material, and then to remove protection from this zone of the preform which it is intended should remain flexible.

In accordance with another embodiment of the invention, the shaping step (machining) follows the structural modification step.

The process of the invention therefore breaks down into four distinct steps:
  premachining step (production of a preform or blank)
  selective impregnation step
  step of modification by chemical reaction and/or polymerization
  step of removing protection or machining (shaping of the preform).

A number of approaches can be used, individually or in combination:
  chemical reaction between a monofunctional or polyfunctional compound and a reactive element of the material of the lens.
  polymerization of one or more monomers within the material of the lens.
  polymerization of a mixture of monomers and polymers outside the material of the lens.

In accordance with a first embodiment of the invention, the anchoring of groups on the material of the lens and/or the formation of an interpenetrated polymer network makes it possible to modify, durably and irreversibly, the characteristics of the modified zone which it is intended should constitute the rigid part, and, in particular, to increase its rigidity (increase in modulus, reduction in hydrophilicity, etc.).

In accordance with another embodiment of the invention, the anchoring of functional groups on the material of the lens allows copolymerization with a mixture of monomers and/or polymers (formation of MOPO).

In the case of MMA-HMA copolymers, for example, it is possible to utilize the reactivity of the hydroxyls of HMA units in order to attach groups capable of modifying the characteristics of the material.

In this case, the possible reactions can be grouped into five categories:

the reactive compound used is monofunctional. Its reaction with the reactive functions of the material of the lens results in chemical modification of the structure of the material and in a decrease in its hydrophilicity. By way of example, mention may be made of functional monomers such as functional styrene derivatives (chloro-methylstyrene, carboxystyrene), acrylic and methacrylic acids and their derivatives (acryloyl and methacryloyl halides, acryloyl and methacryloyl anhydrides), allyl halides, etc. (carboxylic compounds and their derivatives (especially acid halides), isocyanates, alkyl halides, epoxides, etc.)

the reactive compound is polyfunctional. The various functions are antagonistic to the functions of the material of the lens and are capable of reacting with them. This compound then serves as a coupling agent between the different polymer chains of the material. This method permits a reduction in the hydrophilicity of the material and an increase in the crosslinking density, which raises the rigidity of the material. By way of example, mention may be made of divinyl sulfone and its derivatives, (polyfunctional) carboxylic compounds and their derivatives, polyfunctional alkyl halides, di- and tri-isocyanates, polyfunctional epoxides, etc.

the reactive compound used is polyfunctional. One or more of its functions are antagonistic to the functions of the material and are capable of reacting with them. The remaining function or functions is or are polymerizable and allows or allow postpolymerization so as to increase the crosslinking density and raise the rigidity of the material of the lens. By way of example, mention may be made of functional monomers such as functional styrene derivatives (chloromethylstyrene, carboxystyrene, etc.), acryloyl and methacryloyl halides, allyl halides, etc.

the compounds are monomers which impregnate the material and penetrate the network formed by said material. A polymerization reaction then forms interpenetrated networks, thereby increasing the rigidity of the material. By way of example, mention may be made of compounds such as mono- or polyfunctional acrylic and alkylacrylic monomers, heterocyclic monomers such as propylene oxide, etc.

the reactive compound used is polyfunctional. One or more of its functions are antagonistic to the functions of the material and are capable of reacting with them. The remaining function or functions is or are copolymerizable with a mixture of monomers and/or a polymer blend. By way of example, the reactive compound can be methacrylic acid, acrylic acid or an alkylacryloyl halide (methacryloyl chloride in particular), it being possible for the mixture of monomers to be a mixture of styrene, acrylic and alkylacrylic derivatives and it being possible for the polymers to be PMMA, poly(methyl methacrylate-co-styrene), poly(methyl methacrylate-co-alkyl acrylate) and poly(methyl methacrylate-co-alkylacrylate) and poly(methyl methacrylate-co-alkyl alkylacrylate). The monomer mixture/polymer blend is combined with a free-radical initiator.

So as to penetrate the interior of the material, in order to modify it right through, the reactive compounds must, preferably, be miscible with the copolymer chains and must, consequently, possess an appropriate chemical structure.

On premachined lenses it is also possible to carry out surface modification of the zone or zones to be rigidified. Under these conditions, however, the properties obtained are less satisfactory.

The partial and selective impregnation of a specific zone of the lens (which it is intended should become the rigid part) requires the part which it is intended should remain flexible not to be in contact with the reactive compounds. This can be realized in a number of ways:

- in the case of ready-machined lenses, by protecting the part of the lens which it is intended should remain flexible by a temporary impermeable coating, which is subsequently removed;
- in the case of preformed blanks, by an appropriate cutout, which ought to allow rapid impregnation by diffusion of the organic reactive compounds into the zone to be rigidified, which it is intended should become the rigid part, in particular by cutting or premachining thereof. The part which ought to remain flexible, which is not machined, is protected by an overthickness of material, said material preventing the diffusion of the organic reactive compounds to the core of the material which will constitute the flexible part of the lens.

The part which has remained flexible is, finally, exposed by machining following the steps of impregnation and chemical reaction.

In accordance with a first embodiment of the invention, the impregnating step is carried out with an impregnating solution composed, for example, of methacryloyl halide, (in particular, methacryloyl chloride) and a free-radical initiator such as benzoyl peroxide, or of a mixture of methyl methacrylate, acrylic acid, methacryloyl chloride, ethylene glycol dimethacrylate and a free-radical initiator such as azo(bis) isobutyronitrile.

The impregnating step is commonly carried out at ambient temperature, at approximately 20° C., for a period of from 1 h to 48 h, depending on the thickness of the zone to be rigidified, and on the desired rigidity. Increasing the temperature makes it possible to reduce the impregnation time.

In accordance with another embodiment of the invention, the impregnating solution is composed exclusively of a polyfunctional compound such as methacrylic acid or an alkyacryloyl halide (especially methacryloyl chloride).

The modification step is carried out by adding a mixture of monomers and/or a polymer blend in combination with a free-radical initiator. The copolymerization temperature is between 20 and 95° C. for a period of from 1 h to 48 h.

The step of structural modification by chemical reaction and/or polymerization reaction is carried out under an inert atmosphere at a temperature of between 30° C. and 95° C. A pressure of approximately 1 to $5.10^5$ Pa makes it possible to limit the evaporation of the reactants.

The duration of this step is between a few minutes and 48 h, depending on the temperature and on the nature of the catalyst or initiator which is used. The hardness or rigidity which is required for the rigid part is a function of the rate of the chemical modification and/or polymerization reaction.

Regarding the chemical reactions which lead to structural modification of the material, Lewis acids and bases can be used as catalysts. By way of example, mention may be made of the catalysts $BF_3$, $TiCl_4$, amines, etc.

Free-radical polymerization initiators are usually employed for polymerization reactions. By way of example, mention may be made of peroxides, hydroperoxides, percarbonates, redox couples, azonitriles, etc. The initiators used must possess, preferably, a chemical structure which is adapted so as to diffuse into the chains of the material and must have a half-life which is compatible with the chosen polymerization temperature and polymerization time.

The step of removing protection from the protected part of the lens, in the case of premachined lenses, or the machining of the blank, makes it possible to create a nonmodified flexible part and a rigidified zone.

The process of the invention for structural modification by selective rigidification, described above, makes it possible to obtain implants featuring haptic parts having attachment members of various geometric shapes, attachment members having damping elements, or flat haptic parts or other haptic parts of any desired configuration. The haptic parts of the intraocular implants of FIGS. 1 and 2 comprise attachment members.

The lenses are subsequently placed in an aqueous medium in order to induce the swelling of the flexible part and to remove the unreacted products by washing.

The process of the invention will also be described by means of the following nonlimiting examples.

The starting lenses are flexible lenses based on PMMA-PHMA copolymers whose characteristics are as follows:

HMA content: approximately 60 molar %

MMA content: approximately 40 molar % ethylene glycol dimethacrylate: approximately 0.25 molar % in aqueous medium, the degree of swelling is 28%.

EXAMPLE 1

The impregnating solution is composed of 3 ml of methacryloyl chloride. Impregnation is carried out by soaking the preform at 20° C. for from 4 to 24 h depending on the thickness of the part to be rigidified and the rigidity desired.

EXAMPLE 2

The impregnating solution is composed of 3 ml of methacryloyl chloride and 300 mg of benzoyl peroxide. Impregnation is carried out by soaking the preform at 20° C. for from 4 to 24 h depending on the thickness of the part to be rigidified and the rigidity desired.

EXAMPLE 3

The impregnating solution is composed of 1.5 ml of methyl methacrylate, 1.5 ml of methacryloyl chloride and 300 mg of benzoyl peroxide. Impregnation is carried out by soaking the preform at 20° C. for from 4 to 24 h depending on the thickness of the part to be rigidified and the rigidity desired.

EXAMPLE 4

The impregnating solution is composed of 2.7 ml of methacryloyl chloride, 0.3 ml of ethylene glycol dimethacrylate and 300 mg of benzoyl peroxide. Impregnation is carried out by soaking the preform at 20° C. for from 4 to 24 h depending on the thickness of the part to be rigidified and the rigidity desired.

EXAMPLE 5

The impregnating solution is composed of 2.4 ml of acrylic acid, 0.6 ml of methacryloyl chloride and 300 mg of benzoyl peroxide. Impregnation is carried out by soaking the preform at 20° C. for from 4 to 24 h depending on the thickness of the part to be rigidified and the rigidity desired.

EXAMPLE 6

The impregnating solution is composed of 2 ml of methyl methacrylate, 0.7 ml of acrylic acid, 0.3 ml of ethylene glycol dimethacrylate and 300 mg of azo(bis)isobutyronitrile. Impregnation is carried out by soaking the preform at 20° C. for from 4 to 24 h depending on the thickness of the part to be rigidified and the rigidity desired.

The step of structural modification by chemical reaction and/or polymerization is carried out under an inert atmosphere at a pressure of approximately $2.10^5$ Pa. The duration of this step is between 4 and 24 hours depending on the desired rigidity or hardness and in accordance with the amount of polymerization- or reaction-initiating agent which is present in the medium, and in accordance with the desired rigidity for the rigid part.

The step of protecting the flexible part of the lens, in the case of premachined lenses, or the machining of the blank, makes it possible to create a nonmodified part, which has remained flexible, and a zone which has become rigid.

In one embodiment, only the haptic parts or the portions in which the haptic parts are to be formed are impregnated. In a variant embodiment, zones of the optical part adjoining the haptic parts may also be impregnated. Similarly, one or more strips, parallel to a diameter, for example, can be impregnated, strips alternating with the aforementioned strips being protected so as to remain flexible. It will be understood that such strips allow the optical part to be folded or rolled around the zones which have remained flexible.

EXAMPLE 7

The impregnating solution is composed of 1.5 ml of methacryloyl chloride. The duration of impregnation is 4.5 h. The step of copolymerization is carried out by adding a mixture of PMMA and methyl methacrylate, n-butyl methacrylate and benzoyl peroxide.

EXAMPLE 8

The impregnating solution is composed of 1.5 ml of methacryloyl chloride. The duration of impregnation is 4.5 h. The step of copolymerization is carried out by adding a mixture of PMMA and methyl methacrylate, n-butyl methacrylate, hydroxyethyl methacrylate and benzoyl peroxide.

EXAMPLE 9

The impregnating solution is composed of 1.5 ml of methacryloyl chloride. The duration of impregnation is 4.5 h. The step of copolymerization is carried out by adding a mixture of PMMA and methyl methacrylate, n-butyl methacrylate, hydroxyethyl methacrylate, ethylene glycol dimethylacrylate and benzoyl peroxide.

EXAMPLE 10

The impregnating solution is composed of 1.5 ml of methacryloyl chloride. The duration of impregnation is 4.5 h. The step of copolymerization is carried out by adding a mixture of poly(methyl methacrylate-co-styrene), methyl methacrylate, n-butyl methacrylate, ethylene glycol dimethylacrylate and benzoyl peroxide.

EXAMPLE 11

The impregnating solution is composed of 1.5 ml of methacryloyl chloride. The duration of impregnation is 4.5 h. The step of copolymerization is carried out by adding a mixture of poly(methyl methacrylate-co-ethyl acrylate), methyl methacrylate, n-butyl methacrylate, ethylene glycol dimethylacrylate and azo(bis)isobutyronitrile.

EXAMPLE 12

The impregnating solution is composed of 1.5 ml of methacryloyl chloride. The duration of impregnation is 4.5 h. The step of copolymerization is carried out by adding a mixture of poly(methyl methacrylate-co-ethyl methacrylate), methyl methacrylate, n-butyl methacrylate, ethylene glycol dimethylacrylate and benzoyl peroxide.

These examples do not limit the possibilities provided by the present invention. Similarly, the impregnating step can be conducted such that the zones to be treated have a variable hardness as a function, in particular, of the geometry and of the duration of impregnation.

The person skilled in the art will understand that, although the invention has been described and illustrated for specific embodiments, it is possible to envisage numerous variant embodiments while remaining within the scope of the invention as defined in the attached claims.

The invention claimed is:

1. An intraocular lens, comprising a flexible material and at least one relatively rigid material, wherein said flexible material comprises functional groups anchored on the material of the lens which allow copolymerization with a mixture of monomers and/or polymers, thereby resulting in a structural modification which selectively increases the rigidity of the material of the lens.

2. The intraocular lens according to claim 1, wherein the relatively rigid material resulting from a structural chemical modification of said flexible material is a polymerized material.

3. The intraocular lens according to claim 1, wherein the relatively rigid material resulting from a structural chemical modification of said flexible material is hydrophilic.

4. The intraocular lens according to claim 1, wherein the flexible material is selected from the group consisting of crosslinked polymer and copolymer materials.

5. The intraocular lens according to claim 4, wherein the copolymer materials are random methyl-methacrylate-hydroxymethyl-methacrylate (MMA-HMA) co-polymers crosslinked by a functional agent.

6. The intraocular lens according to claim 4, wherein the polymer functional agent is diethylene glycol dimethacrylate.

7. The intraocular lens according to claim 4, wherein the polymer materials are polydimethylsiloxanes.

8. The intraocular lens according to claim 1, wherein said intraocular lens comprises an optic part and a haptic part, said optic part being comprised of said flexible material and said haptic part including said at least one relatively rigid material.

9. The intraocular lens according to claim 1, wherein said intraocular lens comprises an optic part and a haptic part, said optic part comprising one or more portions of the flexible material and one or more portions of the relatively rigid material resulting from a structural chemical modification of said flexible material.

10. The intraocular lens according to claim 1, wherein said intraocular lens comprises an optic part and a haptic part, said optic part comprising one or more strips of the flexible material alternating with one or more strips of the relatively rigid material resulting from a structural chemical modification of said flexible material.

11. The intraocular lens according to claim 1, wherein said intraocular lens comprises an optic part and a haptic part, said optic part including one or more zones adjoining the haptic part and in continuity with one or more zones of the relatively rigid material resulting from a structural chemical modification of said flexible material of the haptic part.

12. The intraocular lens according to claim 11, wherein the haptic part comprises appendices.

13. The intraocular lens according to claim 1, wherein said intraocular lens comprises an optic part and a haptic part, said optic part being primarily made of the flexible material and the haptic part being primarily made of the relatively rigid material resulting from a structural chemical modification of said flexible material.

14. The intraocular lens according to claim 1, wherein the relatively rigid material resulting from a structural chemical modification of said flexible material is a random methyl-methacrylate-hydroxymethyl-methacrylate (MMA-HMA) copolymer modified with at least one reactive compound.

15. The intraocular lens according to claim 14, wherein the reactive compound is a polyfunctional agent, one or more functions of said polyfunctional agent being antagonistic to the functions of MMA-HMA and are capable of reacting with them, the other function or functions of said polyfunctional agent being polymerizable allowing postpolymerization so as to increase crosslinking density and enhance relative rigidity.

16. The intraocular lens according to claim 15, wherein said polyfunctional agent is selected in the group consisting of functional styrene monomer, acryloyl halides, methacryloyl halides, and allyl halides.

17. The intraocular lens according to claim 14, wherein the reactive compound is a polyfunctional agent, one or more functions of said polyfunctional agent being antagonistic to the functions of the HMA and capable of reacting with them, the other function or functions being copolymerizable with a mixture of monomers and/or a polymer blend.

18. The intraocular lens according to claim 17, wherein said polyfunctional agent is selected in the group consisting of methacrylic acid, acrylic acid, and an alkylacryloyl halide.

19. The intraocular lens according to claim 17, wherein the monomers are selected from the group consisting of styrene, acrylic derivatives and alkylacrylic derivatives, and the polymer is PMMA.

20. The intraocular lens according to claim 1, wherein the flexible material has functional groups which are capable of reacting with antagonistic reaction functions of at least one reactive compound, wherein a chemical reaction of said reactive functions with antagonistic reactive functions of at least one reactive compound results in anchoring functional groups on the flexible material.

\* \* \* \* \*